US010570734B2

(12) United States Patent
Rodney et al.

(10) Patent No.: US 10,570,734 B2
(45) Date of Patent: Feb. 25, 2020

(54) DETERMINING CHARACTERISTICS OF A FLUID IN A WELLBORE

(71) Applicant: Halliburton Energy Services, Inc., Houston, TX (US)

(72) Inventors: Paul F. Rodney, Spring, TX (US); Mark W. Roberson, Cary, NC (US); Batakrishna Mandal, Missouri City, TX (US); Vimal V. Shah, Sugarland, TX (US); Scott Goodwin, Chapel Hill, NC (US)

(73) Assignee: Halliburton Energy Services, INC., Houston, TX (US)

( * ) Notice: Subject to any disclaimer, the term of this patent is extended or adjusted under 35 U.S.C. 154(b) by 14 days.

(21) Appl. No.: 15/535,574

(22) PCT Filed: Mar. 11, 2015

(86) PCT No.: PCT/US2015/019845
§ 371 (c)(1),
(2) Date: Jun. 13, 2017

(87) PCT Pub. No.: WO2016/144342
PCT Pub. Date: Sep. 15, 2016

(65) Prior Publication Data
US 2017/0328201 A1    Nov. 16, 2017

(51) Int. Cl.
*G01V 3/20* (2006.01)
*G01V 1/40* (2006.01)
(Continued)

(52) U.S. Cl.
CPC ............ *E21B 49/08* (2013.01); *E21B 47/022* (2013.01); *E21B 47/10* (2013.01); *E21B 47/12* (2013.01);
(Continued)

(58) Field of Classification Search
CPC .......... E21B 47/00; E21B 33/14; E21B 49/00; E21B 47/12; H04L 5/06; G01V 3/20; G01V 1/40
See application file for complete search history.

(56) References Cited

U.S. PATENT DOCUMENTS 4,390,975 A    6/1983  Shawhan
5,148,408 A    9/1992  Matthews
(Continued)

FOREIGN PATENT DOCUMENTS

EP          1335107      10/2008
WO        2014100272     6/2014

OTHER PUBLICATIONS

Barlow et al., Surface Waves, IEEE Radio Section, Paper No. 1482, Apr. 22, 1953, 13 pages.
(Continued)

*Primary Examiner* — Neel D Shah
(74) *Attorney, Agent, or Firm* — Kilpatrick Townsend & Stockton LLP (57) ABSTRACT

An assembly for use in a wellbore can include a plurality of sensors positioned external to a casing string. The plurality of sensors can be positioned for detecting an amount of a hydrocarbon that is present in a fluid in the wellbore and a pH of the fluid in the wellbore. The plurality of sensors can be positioned for wirelessly transmitting signals representing the amount of the hydrocarbon that is present in the fluid and the pH of the fluid to a receiving device.

17 Claims, 5 Drawing Sheets

(51) Int. Cl.
*E21B 49/08* (2006.01)
*E21B 47/10* (2012.01)
*E21B 47/022* (2012.01)
*E21B 47/12* (2012.01)
*G01N 27/30* (2006.01)
*E21B 47/01* (2012.01)

(52) U.S. Cl.
CPC .......... *G01N 27/302* (2013.01); *E21B 47/011* (2013.01); *E21B 2049/085* (2013.01)

(56) References Cited

U.S. PATENT DOCUMENTS

| | | | | |
|---|---|---|---|---|
| 8,007,655 | B2* | 8/2011 | Danyluk | G01N 33/2888 |
| | | | | 204/404 |
| 2003/0112012 | A1* | 6/2003 | Mosley | G01N 27/4167 |
| | | | | 324/446 |
| 2003/0206026 | A1 | 11/2003 | Diakonov et al. | |
| 2004/0252748 | A1 | 12/2004 | Gleitman et al. | |
| 2008/0041721 | A1* | 2/2008 | Hsiung | G01N 27/4167 |
| | | | | 204/415 |
| 2010/0223988 | A1* | 9/2010 | Crow | E21B 41/0064 |
| | | | | 73/152.04 |
| 2010/0286916 | A1* | 11/2010 | Wang | G01V 3/20 |
| | | | | 702/9 |
| 2013/0027042 | A1 | 1/2013 | Meignant et al. | |
| 2013/0176038 | A1 | 7/2013 | Wherritt | |
| 2014/0111349 | A1* | 4/2014 | Roberson | E21B 47/122 |
| | | | | 340/854.8 |
| 2014/0158638 | A1* | 6/2014 | Caulkins | C02F 1/68 |
| | | | | 210/750 |
| 2014/0246237 | A1 | 9/2014 | Prammer | |
| 2015/0046125 | A1* | 2/2015 | Jagiella | G01M 99/005 |
| | | | | 702/184 |
| 2015/0160178 | A1* | 6/2015 | Lee | G01N 33/1886 |
| | | | | 73/61.43 |

OTHER PUBLICATIONS

International Patent Application No. PCT/US2015/019845, International Search Report and Written Opinion, dated Oct. 16, 2015, 16 pages.

Sommerfeld, Über die Fortpflanzung elektrodynamischer Wellen an längs eines Drahtes, Über die Fortpflanzung elektrodynamischer Wellen an längs eines Drahtes, Ann. der Physik und Chemie, vol. 67 (English Translation of title: Propagation of electro-dynamic waves along a cylindric conductor), Dec. 1899, pp. 233-290.

Wikipedia, Surface Wave, retrieved from the internet at http://en.wikipedia.org/wiki/Surface_wave, at least as early as Mar. 16, 2015, 7 pages.

Zenneck, Über die Fortpflanzung ebener elektromagnetischer Wellen längs einer ebenen Leiterfläche und ihre Beziehung zur drahtlosen Telegraphie, Ann. der Physik, vol. 23 (English Translation of title: "About the propagation of electromagnetic plane waves along a conductor plane and their relationship to wireless telegraphy"), Sep. 1907, pp. 846-866.

Australian Application No. AU2015385791, "Third Examination Report", dated Apr. 4, 2019, 6 pages.

West et al., "Metal/Metal Oxide Differential Electrode pH Sensors", Physical Sciences, Available online at <URL:https://www.techbriefs.com/component/content/article/tb/techbriefs/physical-sciences/2287 >, Oct. 1, 2007, 4 pages.

\* cited by examiner

DETERMINING CHARACTERISTICS OF A FLUID IN A WELLBORE

CROSS-REFERENCE TO RELATED APPLICATIONS

This is a U.S. national phase under 35 U.S.C. 371 of International Patent Application No. PCT/US2015/019845 titled "Determining Characteristics Of A Fluid In A Wellbore" and filed Nov. 11, 2015, the entirety of which is incorporated herein by reference.

TECHNICAL FIELD

The present disclosure relates generally to devices for use in well systems. More specifically, but not by way of limitation, this disclosure relates to determining characteristics of a fluid in a wellbore.

BACKGROUND

A well system (e.g., an oil or gas well) can include a wellbore that is typically drilled for extracting hydrocarbons from a subterranean formation. To determine information about the well system (e.g., such as the commercial viability of the well system), it may be desirable to analyze fluid in the wellbore. It may be challenging, however, to analyze fluid in the wellbore.

DETAILED DESCRIPTION

Certain aspects and features of the present disclosure are directed to determining characteristics of a fluid (e.g., cement) in a wellbore. In some examples, a sensor is positioned external to a casing string in the wellbore or floating within the fluid in the wellbore. A sensor can be positioned external to the casing string if it is positioned on or external to an outer diameter or outer wall of the casing string. The sensor can detect an amount of a hydrocarbon in the wellbore, a pH of a fluid in the wellbore, an inclination of the wellbore, or any combination of these well system characteristics. The sensor can transmit data associated with the well system characteristics (e.g., the amount of the hydrocarbon present in the wellbore) to a receiver via a wired or wireless communications interface.

In some examples, the sensor can include a hydrocarbon sensor. The hydrocarbon sensor can determine the presence of (and an amount of) a hydrocarbon in the wellbore. In some examples, the hydrocarbon sensor can include two conductive electrodes positioned in parallel and with a gap between the two conductive electrodes. The gap can form a fluid communication path through which the fluid in the wellbore can flow. The combination of the two conductive electrodes with the fluid can form a capacitor in which the fluid is the dielectric material. Upon applying electricity across the two conductive electrodes, the sensor can measure an electrical characteristic (e.g., a capacitance, an impedance, or the frequency of an oscillating waveform) associated with the two conductive electrodes. The electrical characteristic can change based on the dielectric properties of the fluid (e.g., the type of the fluid). The sensor can determine, based on the electrical characteristic, whether a hydrocarbon is present in the fluid (and what type of hydrocarbon is present in the fluid).

In some examples, the sensor can include one or more pH sensors. The pH sensors can detect the pH of the fluid in the wellbore. A pH sensor can include two different conductive materials, each coupled to a voltage-comparing device (e.g., a comparator, a voltmeter, a computing device, or other voltage comparison circuitry). Upon the fluid in the wellbore contacting the two difference conductive materials, a voltage can be generated across the conductive materials. The voltage-comparing device can compare a voltage generated across the two conductive materials to a reference voltage to determine the pH of the fluid. In other examples, the pH sensor can include an ionic sensor coupled to a voltage-comparing device. The voltage-comparing device can compare a voltage generated by the ionic sensor to a reference voltage to determine the pH of the fluid.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

Figure 1:
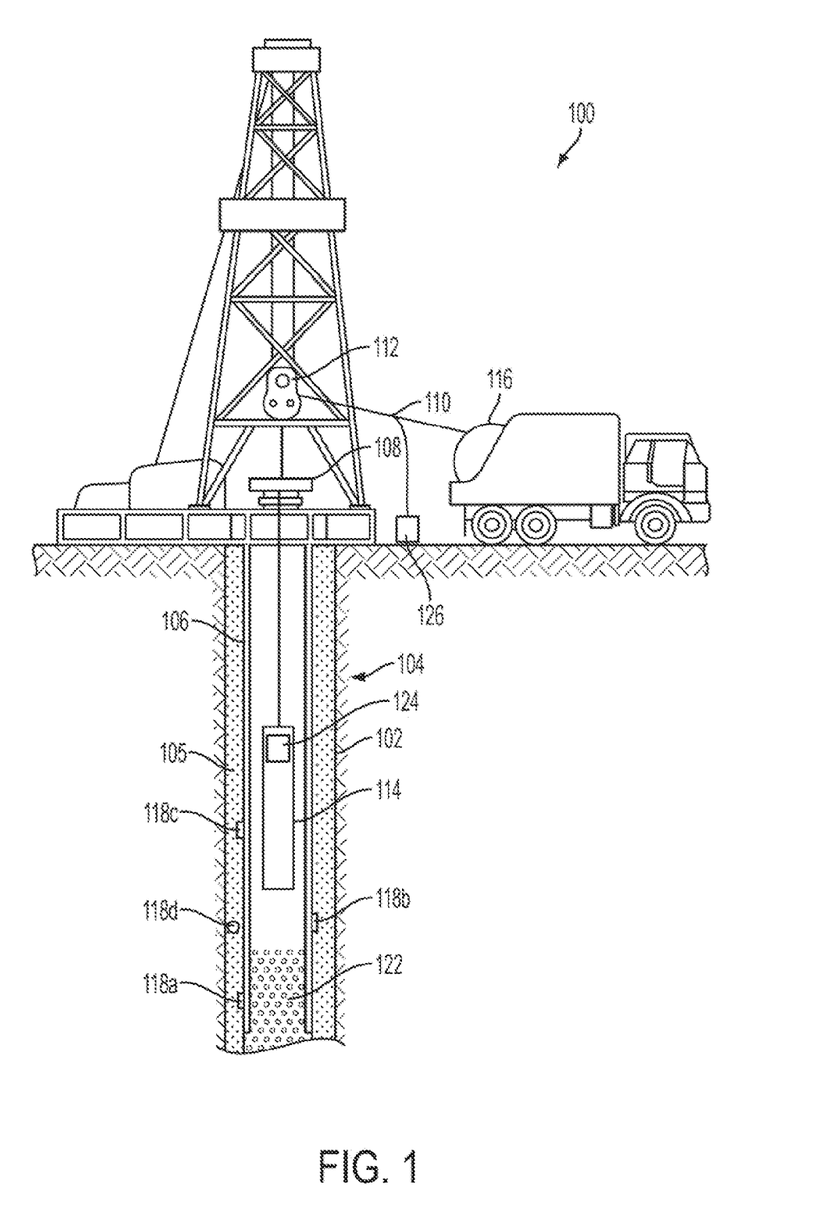
FIG. 1 is a cross-sectional view of an example of a well system that includes a system for determining characteristics of a fluid in a wellbore.

FIG. 1 is a cross-sectional view of an example of a well system 100 that includes a system for determining characteristics of a fluid in a wellbore. The well system 100 includes a wellbore 102 extending through various earth strata. The wellbore 102 extends through a hydrocarbon bearing subterranean formation 104. A casing string 106 extends from the surface 108 to the subterranean formation 104. The casing string 106 can provide a conduit through which fluid 122, such as production fluids produced from the subterranean formation 104, can travel from the wellbore 102 to the surface 108. The casing string 106 can be coupled to the walls of the wellbore 102. For example, a fluid 105 (e.g., cement) can be pumped between the casing string 106 and the walls of the wellbore 102 for coupling the casing string 106 to the wellbore 102.

The well system 100 can also include at least one well tool 114 (e.g., a formation-testing tool). The well tool 114 can be coupled to a wireline 110, slickline, or coiled tube that can be deployed into the wellbore 102. The wireline 110, slickline, or coiled tube can be guided into the wellbore 102 using, for example, using a guide 112 or winch. In some examples, the wireline 110, slickline, or coiled tube can be wound around a reel 116.

The well system 100 can include one or more sensors 118a-d. In some examples, the sensors 118a-d can include a protective housing (e.g., a fluid resistant housing). This can prevent the sensors 118a-d from being damaged by fluid 105, 122, the well tool 114, and debris downhole.

In some examples, a sensor 118a can include an inclinometer. The inclinometer can determine the inclination of the well system 100 (e.g., by detecting the inclination of the casing string 106 to which the sensor 118a can be coupled). This can be particularly useful if the well system 100 is an angled well system (e.g., the wellbore 102 is drilled at an angle between 0 and 90 degrees). Additionally or alternatively, a sensor 118a can include a pH sensor. The pH sensor can determine the pH of one or more fluids 105, 122 in the wellbore 102. Examples of pH sensors are further described with respect to FIG. 2. In some examples, the sensor 118a can additionally or alternatively include a hydrocarbon sensor. The hydrocarbon sensor can detect the presence of, or a characteristic of, a hydrocarbon in the wellbore 102. An example of a hydrocarbon sensor is further described with respect to FIG. 4.

In some examples, the sensors 118a-d can be coupled external to the casing string 106. This can allow the sensors 118a-d to monitor the characteristics of the well system 100, even if the well tool 114 is removed or changed. For example, the sensors 118a-d can be positioned external to an outer housing of, or partially embedded within, the casing string 106. In other examples, the sensors 118a-d can be configured to float within or near the surface of a fluid 105, 122 in the wellbore 102. For example, as shown in FIG. 1, sensor 118d is floating near the within the fluid 105 in the wellbore 102.

In some examples, the sensors 118a-d can transmit data (e.g., via wires or wirelessly) associated with the characteristics of the wellbore 102, the fluid 105, 122, or both to a receiver 124 (or to another one of the sensors 118a-d). The sensors 118a-d can transmit and receive data using a transceiver, as described in greater detail with respect to FIG. 2. In some examples, the sensors 118a-d can transmit data using very low frequency (VLF) magnetic or current pulses, ultrasonic pulses, acoustic pulses, electromagnetic coupling, inductive coupling, or any combination of these.

One or more receivers 124, 126 can be positioned in the well system 100 for receiving data from the sensors 118a-d. In some examples, the receivers 124, 126 can be positioned on the well tool 114, on the casing string 106, or at the surface 108 of the well system 100. The receivers 124, 126 can directly or indirectly receive the data from the sensors 118a-d (or other receivers) via a transceiver (which can be substantially the same as transceiver 216 of FIG. 2). For example, a receiver 124 can wirelessly receive data from a sensor 118a. The receiver 124 can then relay the data via wireline 110 to another receiver 126 at the surface 108. In some examples, the receiver 124 can include a distributed acoustic sensor (DAS). A DAS can include a fiber-optic device configured to detect acoustic transmissions (e.g., acoustic emissions) from the sensors 118a-d. In some examples, the receiver 124 can use the DAS to receive (e.g., detect) acoustic transmissions from the sensor 118a-d.

Figure 2:
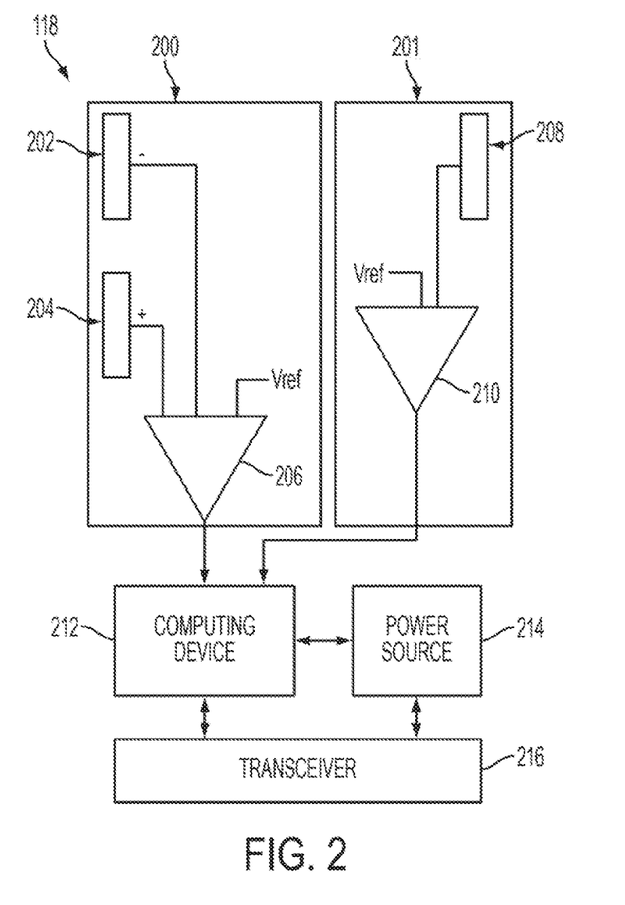
FIG. 2 is a block diagram of an example of a sensor for determining characteristics of a fluid in a wellbore.

FIG. 2 is a block diagram of an example of a sensor 118 for determining characteristics of a fluid in a wellbore. In some examples, the components shown in FIG. 2 (e.g., the computing device 212, power source 214, transceiver 216, pH sensor 200, and pH sensor 201) can be integrated into a single structure. For example, the components can be within a single housing. In other examples, the components shown in FIG. 2 can be distributed (e.g., in separate housings) and in electrical communication with each other.

The sensor 118 can include a pH sensor 200. The pH sensor 200 can include two electrodes 202, 204. The electrodes 202, 204 can include different conductive materials (e.g., different types of metal). For example, one electrode 202 can include copper and the other electrode 204 can include gold. The electrodes 202, 204 can be exposed for contacting fluid (e.g., cement) in a wellbore. Upon a fluid contacting the electrodes 202, 204, a voltage can be generated between the electrodes 202, 204. The amount of voltage generated between the electrodes 202, 204 can depend on the pH of the fluid. A comparator 206 can compare the voltage generated between the electrodes 202, 204 to a reference voltage (e.g., Vref) to determine whether the voltage generated between the electrodes 202, 204 is larger or smaller than the reference voltage. In some examples, the reference voltage can be calibrated such that the voltage generated between the electrodes 202, 204 is larger than the reference voltage when the fluid contains a particular pH level or is above a threshold pH level. In some examples, the comparator 206 can transmit a signal associated with the comparison of the voltages to a computing device 212. The computing device 212 can receive the signal and determine the pH of the fluid based on the signal.

The sensor 118 can additionally or alternatively include another pH sensor 201. The other pH sensor can include an ionic sensor 208. An ionic sensor 208 can convert the activity of a specific ion dissolved in a fluid into electrical potential (e.g., voltage). Upon a fluid contacting the ionic sensor 208, a voltage can be generated that can be transmitted to a comparator 210. The comparator 210 can compare the voltage generated by the ionic sensor 208 to a reference voltage. In some examples, the reference voltage can be calibrated such that the voltage generated by the ionic sensor 208 is larger than the reference voltage when the fluid contains a particular pH level or is above a threshold pH level. In some examples, the comparator 210 can transmit a signal associated with the comparison of the voltages to a computing device 212. The computing device 212 can receive the signal and determine the pH of the fluid based on the signal.

In some examples, the sensor 118 can use both pH sensors 200, 201 to determine the pH of the fluid. For example, the computing device 212 can receive signals from both pH sensors 200, 201 and compare the signals. If the signals from both pH sensors 200, 201 indicate substantially the same pH level, the sensor 118 (e.g., the computing device 212) can determine that the pH measurements are accurate. If the signals from the pH sensors 200, 201 indicate different pH levels, the sensor 118 can determine that an error occurred. This may provide redundancy, improving the accuracy of the sensor 118.

In some examples, the comparators 206, 210 can be replaced with voltmeters or other voltage measurement circuitry. For example, the comparator 206 can be replaced with a voltmeter configured to detect the voltage between the electrodes 202, 204. The voltmeter can transmit a signal associated with the detected voltage to the computing device 212. As another example, the comparator 210 can be replaced with a voltmeter configured to detect a voltage generated by the ionic sensor 208 and transmit a signal associated with the detected voltage to the computing device 212. The computing device 212 can receive the signals from the voltmeters (or other voltage measurement circuitry) and determine a pH of the fluid based on the signals. For example, the computing device 212 can use a lookup table to associate a voltage (e.g., from a voltmeter) with a predetermined voltage of a fluid with a particular pH level.

In some examples, the voltage generated by at least one of the pH sensors 200, 201 can be applied to the computing device 212, the transceiver 216, or both. This voltage can power the computing device 212, the transceiver 216, or both. In other examples, components of the sensor 118 (e.g., the computing device 212, the transceiver 216, or both) can be powered by a power source 214. In some examples, the power source 214 can include a battery or a wired interface coupled to an electrical source. The power source 214 can be in electrical communication with the computing device 212, and the transceiver 216, and other components of the sensor 118.

In some examples, the computing device 212 can record (e.g., in memory 308 of FIG. 3) the pH of the fluid sensed by the sensor 118. Additionally or alternatively, the computing device 212 can transmit (e.g., wired or wirelessly) a signal associated with a fluid characteristic (e.g., the pH of a fluid, or an amount of a hydrocarbon), a wellbore characteristic, or both via a transceiver 216.

The sensor 118 can transmit and receive data via the transceiver 216. The transceiver 216 can represent any components that facilitate a network connection. In some examples, the transceiver 216 can be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). Further, in some examples, the transceiver 216 can wirelessly transmit data using very low frequency (VLF) magnetic or current pulses, ultrasonic pulses, acoustic pulses, electromagnetic coupling, inductive coupling, or any combination of these. In other examples, the transceiver 216 can be wired and can include interfaces such as Ethernet, USB, IEEE 1394, or a fiber optic interface.

Figure 3:
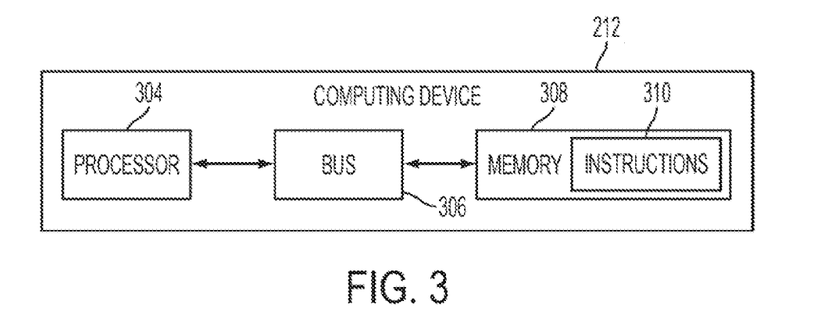
FIG. 3 is a block diagram of an example of a computing device for determining characteristics of a fluid in a wellbore.

FIG. 3 is a block diagram of an example of a computing device 212 for determining characteristics of a fluid in a wellbore. The computing device 212 can include a processor 304, a memory 308, and a bus 306. The processor 304 can execute one or more operations for operating a transceiver. The processor 304 can execute instructions 310 stored in the memory 308 to perform the operations. The processor 304 can include one processing device or multiple processing devices. Non-limiting examples of the processor 304 include a Field-Programmable Gate Array ("FPGA"), an application-specific integrated circuit ("ASIC"), a microprocessor, etc.

The processor 304 can be communicatively coupled to the memory 308 via the bus 306. The non-volatile memory 308 may include any type of memory device that retains stored information when powered off. Non-limiting examples of the memory 308 include electrically erasable and programmable read-only memory ("EEPROM"), flash memory, or any other type of non-volatile memory. In some examples, at least some of the memory 308 can include a medium from which the processor 304 can read the instructions 310. A computer-readable medium can include electronic, optical, magnetic, or other storage devices capable of providing the processor 304 with computer-readable instructions or other program code. Non-limiting examples of a computer-readable medium include (but are not limited to) magnetic disk(s), memory chip(s), ROM, random-access memory ("RAM"), an ASIC, a configured processor, optical storage, or any other medium from which a computer processor can read instructions. The instructions can include processor-specific instructions generated by a compiler or an interpreter from code written in any suitable computer-programming language, including, for example, C, C++, C#, etc.

Figure 4:
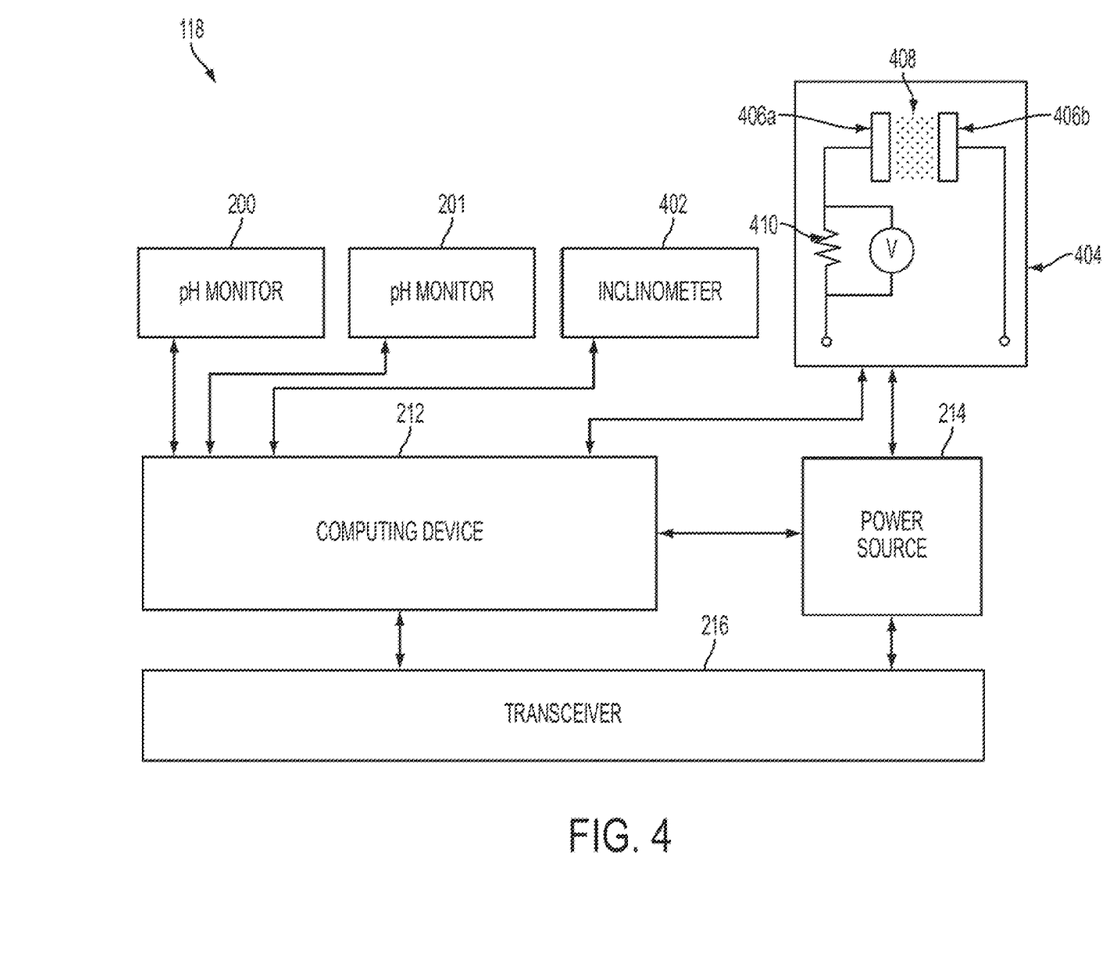
FIG. 4 is a block diagram of an example of a sensor for determining characteristics of a fluid in a wellbore.

FIG. 4 is a block diagram of an example of a sensor 118 for determining characteristics of a fluid 408 in a wellbore. In this example, the sensor 118 includes a pH sensor 200, another pH sensor 201, an inclinometer 402, and a hydrocarbon sensor 404.

The hydrocarbon sensor 404 can detect the presence of a hydrocarbon in the wellbore. In some examples, the hydrocarbon sensor 404 can detect the presence of a hydrocarbon by measuring a dielectric constant of a fluid 408 in the wellbore. Based on the dielectric constant, the sensor 118 can determine if the fluid 408 is water, cement, or a hydrocarbon.

For example, the hydrocarbon sensor 404 can include two electrodes 406a, 406b. The electrodes 406a, 406b can include any suitable conductive material, such as gold, silver, copper, or lead. The two electrodes 406a, 406b can be positioned parallel to each other with a gap between the electrodes 406a, 406b (e.g., arranged similar to capacitor plates). The gap can provide a fluid communication path through which fluid 408 can flow or otherwise be positioned between the parallel electrodes 406a, 406b. The fluid 408 between the electrodes 406a, 406b can act as a dielectric material. The combination of the parallel electrodes 406a, 406b and the fluid 408 acting as a dielectric can create a capacitor. In some examples, the sensor 118 (e.g., via the computing device 212 or the power source 214) can apply a power signal to the electrodes 406a, 406b. The frequency of the power signal can be within the microwave range of frequencies. This can generate an amount of capacitance across the electrodes 406a, 406b that is based on the dielectric constant of the fluid 408. In some examples, the sensor 118 can measure the capacitance and, based on the capacitance, can determine the type of the fluid (e.g., whether the fluid is a hydrocarbon or water).

In some examples, a resistor 410 can be positioned in series with the capacitor (e.g., the electrodes 406a, 406b and the fluid 408) in the hydrocarbon sensor 404. This can create a series RC electrical circuit. Upon applying power to the electrodes 406a, 406b, the sensor 118 can measure a voltage across the resistor (e.g., using a voltmeter coupled across the resistor). Based on the voltage, the sensor 118 can determine an impedance. Based on the impedance of the capacitor, the sensor 118 can determine the type of fluid 408 between the plates.

In still other examples, an inductor (L) can be positioned in series with the capacitor (e.g., the electrodes 406a, 406b and the fluid 408). This can create a series LC electrical circuit. In some examples, the LC circuit can be configured to resonate when the fluid 408 contains a particular hydrocarbon. For example, the inductor can be tuned such that the inductive reactance and the capacitive reactance are equal when the fluid 408 includes a particular hydrocarbon. In some examples, the sensor 118 can detect whether the LC circuit is resonating and, based on this detection, determine whether the fluid 408 includes a particular hydrocarbon.

In some examples, the hydrocarbon sensor 404 can include an ionic sensor (not shown). As discussed above, an ionic sensor can convert the activity of a specific ion dissolved in a fluid into voltage. Because different fluids can have different levels and types of ions dissolved in the fluids, different fluids can cause the ionic sensor to generate different voltage levels. In some examples, the sensor 118 can determine, based on the voltage level from the ionic sensor, the type of fluid in the wellbore. For example, the computing device 212 can consult a lookup table (e.g., stored in memory) to determine a fluid in the wellbore using a voltage level from the hydrocarbon sensor 404.

In some examples, the hydrocarbon sensor 404 can use a solid state device with a P-N junction and the ionic concentrations of a fluid in the wellbore to determine a characteristic of the fluid. For example, the hydrocarbon sensor can include an ion-sensitive field-effect transistor (ISFET). The ISFET can be configured to use the fluid (e.g., a sample of the fluid) as the gate electrode. Upon an ion concentration in the fluid changing, current flowing through the ISFET can change. In some examples, the sensor 118 can measure the current flowing through the ISFET and determine, based on a change in the current, the ionic concentration of the fluid. The sensor 118 can determine, based on the ionic concentration, the type of the fluid in the wellbore. In other examples, the hydrocarbon sensor 404 can use infrared absorption, or the chemical interaction with a metal junction, to determine ionic concentration. From the ionic concentration, the sensor 118 can determine the type of the fluid in the wellbore.

In some examples, the sensor 118 can determine the cumulative concentration of a hydrocarbon in a fluid. For example, the sensor 118 can determine the cumulative concentration of the hydrocarbon in the fluid by integrating instantaneous concentrations of the hydrocarbon over time: ∫HydrocarbonConcentration (dt). As another example, the sensor 118 can determine the cumulative concentrations of the hydrocarbon by summing instantaneous concentrations of the hydrocarbon over time: ΣHydrocarbonConcentration*i*Δt, where Δt can represent a change in time.

Figure 5:
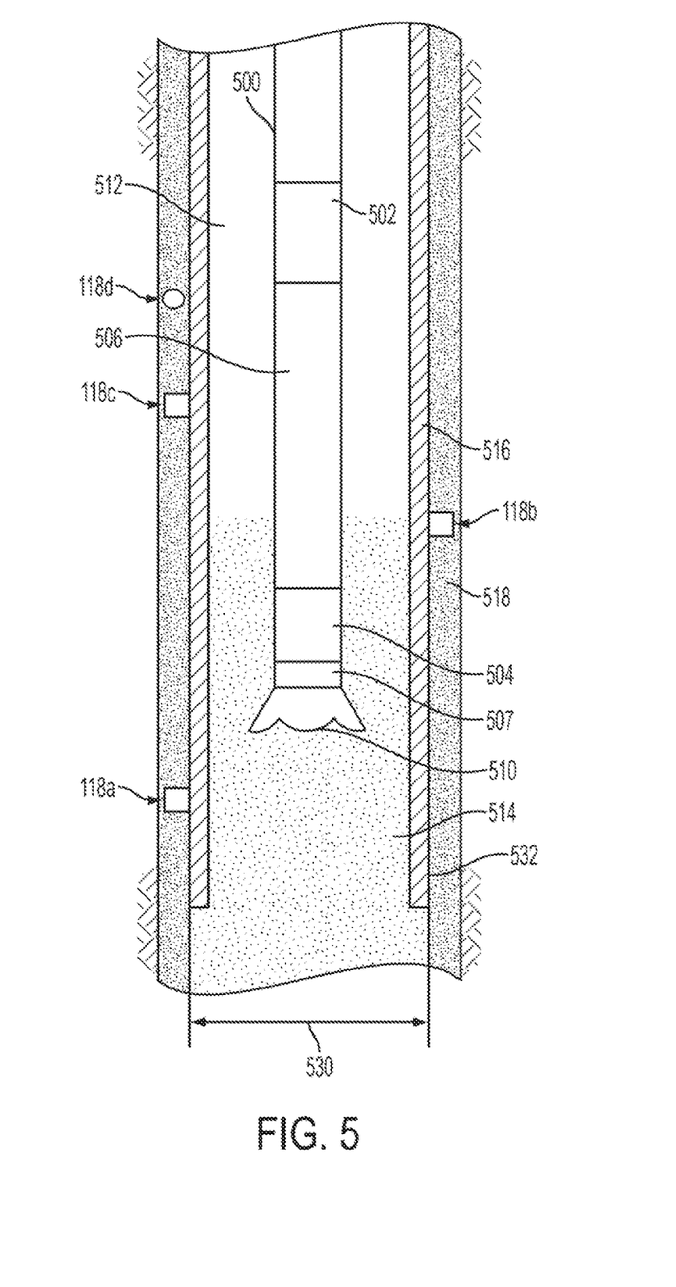
FIG. 5 is another cross-sectional view of an example of a well system that includes a system for determining characteristics of a fluid in a wellbore.

FIG. 5 is another cross-sectional view of an example of a well system that includes a system for determining characteristics of a fluid 514 in a wellbore. In this example, the well system includes a wellbore. The wellbore can include a casing string 516 and a fluid 518 (e.g., cement) between the casing string 516 and a wall of the wellbore. In some examples, the wellbore can include a fluid 514 (e.g., mud, cement, or a hydrocarbon) that can flow in an annulus 512 positioned between a well tool 500 and a wall of the casing string 516.

A well tool 500 (e.g., logging-while-drilling tool) can be positioned in the wellbore. The well tool 500 can include various subsystems 502, 504, 506, 507. For example, the well tool 500 can include a subsystem 502 that includes a communication subsystem. The well tool 500 can also include a subsystem 504 that includes a saver subsystem or a rotary steerable system. A tubular section or an intermediate subsystem 506 (e.g., a mud motor or measuring-while-drilling module) can be positioned between the other subsystems 502, 504. In some examples, the well tool 500 can include a drill bit 510 for drilling the wellbore. The drill bit 510 can be coupled to another tubular section or intermediate subsystem 507 (e.g., a measuring-while-drilling module or a rotary steerable system).

The well system can also include sensors 118a-d. The sensors 118a-d can be positioned external to the casing string 516 (e.g., external to an outer diameter 530 of the casing string 516). For example, the sensors 118a-d can be positioned on an outer housing 532 of the casing string 516. As discussed above, the sensors 118a-d can include an inclinometer, a pH sensor, a hydrocarbon sensor, or any combination of these. The sensors 118a-d can detect characteristics of the fluid 518, 514, the wellbore, or both and transmit data associated with the characteristics (e.g., to a receiver).

Figure 6:
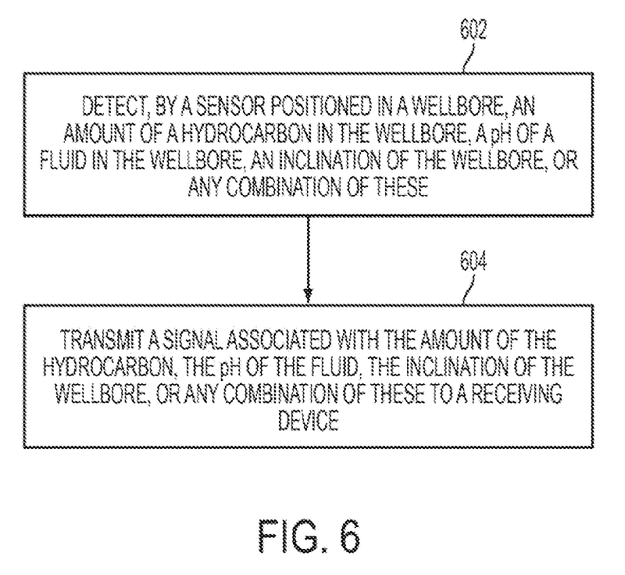
FIG. 6 is a flow chart showing an example of a process for determining characteristics of a fluid in a wellbore.

FIG. 6 is a flow chart showing an example of a process for determining characteristics of a fluid in a wellbore according to one example.

In block 602, a sensor positioned in a wellbore detects an amount of a hydrocarbon in the wellbore, a pH of a fluid (e.g., cement) in the wellbore, an inclination of the wellbore, or any combination of these. The sensor can be positioned external to an outer diameter of a casing string.

In some examples, the sensor can include a hydrocarbon sensor. The sensor can use the hydrocarbon sensor to determine the amount of the hydrocarbon in the wellbore. In some examples, the hydrocarbon sensor can include two conductive electrodes positioned in parallel and with a gap between the two conductive electrodes. The gap can form a fluid communication path through which the fluid in can flow. In some examples, a sample of the fluid can be positioned in the gap for a period of time (e.g., the sensor can take a sample of the fluid and position the fluid in the gap). Upon applying electricity across the two conductive electrodes, the sensor can measure an electrical characteristic (e.g., a capacitance, impedance, or the frequency of an oscillating waveform) associated with the two conductive electrodes. The sensor can determine, based on the electrical characteristic, whether a hydrocarbon is present in the fluid (and what type of hydrocarbon is present in the fluid).

In some examples, the sensor can include one or more pH sensors. The pH sensors can detect the pH of the fluid in the wellbore. In some examples, a pH sensor can include two different conductive materials each coupled to a voltage detection device (e.g., a voltmeter, a computing device, or other voltage detection circuitry). Using the voltage detection device, the sensor can detect an amount of voltage generated across the two different conductive materials. Based on the detected amount of voltage, the sensor can determine the pH of the fluid. In other examples, the pH sensor can include an ionic sensor coupled to a voltage detection device. The sensor can use the voltage detection device to detect an amount of voltage generated by the ionic sensor. Based on the detected amount of voltage, the sensor can determine the pH of the fluid.

In some examples, the sensor can include an inclinometer. The inclinometer can detect the inclination of the wellbore or a well system component (e.g., a casing string to which the sensor may be coupled).

In block 604, the sensor transmits a signal associated with the amount of the hydrocarbon, the pH of the fluid, the inclination of the wellbore, or any combination of these to a receiving device. The sensor can transmit the signal wirelessly or via a wired interface. In some examples, the receiving device can include a DAS sensor. In some examples, the receiving device can be positioned on or within a well tool in the wellbore, on a cement casing of the wellbore, or at the surface of the wellbore. In other examples, the receiving device can be positioned elsewhere in the well system.

In some aspects, systems and methods for determining characteristics of a fluid in a wellbore are provided according to one or more of the following examples:

Example #1

A system for use in a wellbore can include a plurality of sensors positioned external to a casing string for detecting an amount of a hydrocarbon that is present in a fluid in the wellbore and a pH of the fluid in the wellbore. The plurality of sensors can wirelessly transmitting signals representing the amount of the hydrocarbon that is present in the fluid and the pH of the fluid to a receiving device.

Example #2

The system of Example #1 may feature the plurality of sensors including a hydrocarbon sensor. The hydrocarbon sensor can include two conductive electrodes positioned in parallel and with a gap between the two conductive electrodes. The gap can form a fluid communication path for the fluid to flow.

Example #3

The system of any of Examples #1-2 may feature a hydrocarbon sensor that includes a processing device and a memory device. The memory device can store instructions executable by the processing device for causing the processing device to: transmit a power signal with a frequency that is within a microwave range of frequencies to two conductive electrodes; detect an electrical characteristic associated with the two conductive electrodes; and determine a type of the fluid based on the electrical characteristic.

Example #4

The system of any of Examples #1-3 may feature the plurality of sensors including a pH sensor. The pH sensor can include two different conductive materials each coupled to a voltage-comparing device to compare a voltage generated across the two different conductive materials to a reference voltage to determine the pH of the fluid.

Example #5

The system of any of Examples #1-4 may feature the plurality of sensors including a pH sensor. The pH sensor can include an ionic sensor coupled to a voltage-comparing device to compare a voltage generated by the ionic sensor to a reference voltage to determine the pH of the fluid.

Example #6

The system of any of Examples #1-5 may feature the plurality of sensors including an inclinometer to detect an inclination of the casing string and to wirelessly transmit another signal representing the amount of the inclination to the receiving device.

Example #7

A system can include a first sensor that is arranged to float in a fluid in a wellbore for detecting an amount of a hydrocarbon that is present in the fluid and for wirelessly transmitting a signal representing the amount of the hydrocarbon that is present in the fluid to a receiving device. The system can also include a second sensor positioned external to a casing string for detecting a pH of the fluid and for wirelessly transmitting another signal representing the pH of the fluid to the receiving device.

Example #8

The system of Example #7 may feature the first sensor including a hydrocarbon sensor. The hydrocarbon sensor can include two conductive electrodes positioned in parallel and with a gap between the two conductive electrodes. The gap can form a fluid communication path for the fluid to flow.

Example #9

The system of any of Examples #7-8 may feature a hydrocarbon sensor that includes a processing device and a memory device. The memory device can store instructions executable by the processing device for causing the processing device to: transmit a power signal with a frequency that is within a microwave range of frequencies to two conductive electrodes; detect an electrical characteristic associated with the two conductive electrodes; and determine a type of the fluid based on the electrical characteristic.

Example #10

The system of any of Examples #7-9 may feature second sensor including a pH sensor. The pH sensor can include two different conductive materials each coupled to a voltage-comparing device to compare a voltage generated across the two different conductive materials to a reference voltage to determine the pH of the fluid.

Example #11

The system of any of Examples #7-10 may feature the second sensor including a pH sensor that includes an ionic sensor coupled to a voltage-comparing device to compare a voltage generated by the ionic sensor to a reference voltage to determine the pH of the fluid.

Example #12

The system of any of Examples #7-11 may feature a third sensor positioned on an outer housing of the casing string to detect an inclination of the casing string and to wirelessly transmit another signal representing the amount of the inclination to the receiving device.

Example #13

A system can include a plurality of sensors positioned on an outer housing of a casing string for detecting an amount of a hydrocarbon fluid in a wellbore and an inclination of the casing string, and for wirelessly transmit signals representing the amount of the hydrocarbon fluid and the inclination to a receiving device.

Example #14

The system of Example #13 may feature the plurality of sensors including a hydrocarbon sensor. The hydrocarbon sensor can include two conductive electrodes positioned in parallel and with a gap between the two conductive electrodes. The gap can form a fluid communication path for a fluid to flow.

Example #15

The system of any of Examples #13-14 may feature a hydrocarbon sensor that includes a processing device and a memory device. The memory device can store instructions executable by the processing device for causing the processing device to: transmit a power signal with a frequency that is within a microwave range of frequencies to two conductive electrodes; detect an electrical characteristic associated with the two conductive electrodes; and determine a type of the fluid based on the electrical characteristic.

Example #16

The system of any of Examples #13-15 may feature the plurality of sensors including a pH sensor. The pH sensor can include two different conductive materials each coupled to a voltage-comparing device to compare a voltage generated across the two different conductive materials to a reference voltage to determine the pH of the fluid.

Example #17

The system of any of Examples #13-16 may feature the plurality of sensors including a pH sensor that includes an ionic sensor coupled to a voltage-comparing device to compare a voltage generated by the ionic sensor to a reference voltage to determine the pH of the fluid.

Example #18

The system of any of Examples #13-17 may feature each of the plurality of sensors including a hydrocarbon sensor and an inclinometer.

Example #19

The system of any of Examples #13-18 may feature each of the plurality of sensors including a pH sensor, an inclinometer, and a hydrocarbon sensor.

Example #20

The system of any of Examples #13-19 may feature the receiving device being positionable in a well tool.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system for use in a wellbore, the system comprising:
    a plurality of sensors positioned external to a casing string for detecting an amount of a hydrocarbon that is present in a fluid in the wellbore and a pH of the fluid in the wellbore, and for wirelessly transmitting signals representing the amount of the hydrocarbon that is present in the fluid and the pH of the fluid to a receiving device,
    wherein at least one sensor of the plurality of sensors includes a pH sensor, a computing device, and a transceiver; and
    wherein the pH sensor is configured to supply voltage to a power port of the computing device or the transceiver to power the computing device or the transceiver.

2. The system of claim 1, wherein the plurality of sensors comprises a hydrocarbon sensor that includes two conductive electrodes positioned in parallel and with a gap between the two conductive electrodes, wherein the gap forms a fluid communication path for the fluid to flow.

3. The system of claim 2, wherein the hydrocarbon sensor comprises:
    a processing device; and
    a memory device in which instructions executable by the processing device are stored for causing the processing device to:
        transmit a power signal with a frequency that is within a microwave range of frequencies to the two conductive electrodes;
        detect an electrical characteristic associated with the two conductive electrodes; and
        determine a type of the fluid based on the electrical characteristic.

4. The system of claim 2, wherein hydrocarbon sensor includes an inductor that is electrically coupled in series to a capacitor to form an inductor-capacitor (LC) circuit, the LC circuit being tuned to resonate when the fluid in the fluid communication path is a particular type of hydrocarbon.

5. The system of claim 1, wherein the pH sensor includes two different conductive materials each coupled to a voltage-comparing device to compare a voltage generated across the two different conductive materials to a reference voltage to determine the pH of the fluid.

6. The system of claim 1, wherein the pH sensor includes a comparator, the comparator being configured to compare a voltage generated by the pH sensor to a reference voltage to produce an output voltage, the output voltage being the voltage provided to the power port to power the computing device or transceiver.

7. The system of claim 1, wherein the plurality of sensors comprises an inclinometer to detect an inclination of the casing string and to wirelessly transmit another signal representing the amount of the inclination to the receiving device.

8. The system of claim 1, wherein:
    the pH sensor is a first pH sensor,
    the at least one sensor includes a second pH sensor, and
    the computing device is configured to:
        receive a first sensor signal from the first pH sensor and a second sensor signal from the second pH sensor;
        determine that a first pH level represented by the first sensor signal is substantially similar to a second pH level represented by the second sensor signal; and
        in response to determining that the first PH level is substantially similar to the second pH level, determining that the first pH level is accurate.

9. The system of claim 1, wherein the pH sensor is configured to power the computing device or the transceiver as an alternative to a power source.

10. A system comprising:
    a plurality of sensors positionable on an outer housing of a casing string for detecting an amount of a hydrocarbon fluid in a wellbore and an inclination of the casing string, and for wirelessly transmit signals representing the amount of the hydrocarbon fluid and the inclination to a receiving device;
    wherein at least one sensor of the plurality of sensors includes a pH sensor, a computing device, and a transceiver; and
    wherein the pH sensor is configured to supply voltage to a power port of the computing device or the transceiver to power the computing device or the transceiver.

11. The system of claim 10, wherein the plurality of sensors comprises a hydrocarbon sensor that includes two conductive electrodes positioned in parallel and with a gap between the two conductive electrodes, wherein the gap forms a fluid communication path for a fluid to flow.

12. The system of claim 11, wherein the hydrocarbon sensor comprises:
    a processing device; and
    a memory device in which instructions executable by the processing device are stored for causing the processing device to:
        transmit a power signal with a frequency that is within a microwave range of frequencies to the two conductive electrodes;
        detect an electrical characteristic associated with the two conductive electrodes; and
        determine a type of the fluid based on the electrical characteristic.

13. The system of claim 10, wherein the at least one sensor includes two different conductive materials each coupled to a voltage-comparing device to compare a voltage generated across the two different conductive materials to a reference voltage to determine a pH of a fluid.

14. The system of claim 10, wherein the at least one sensor includes an ionic sensor coupled to a voltage-comparing device to compare a voltage generated by the ionic sensor to a reference voltage to determine a pH of a fluid.

15. The system of claim 10, wherein each of the plurality of sensors comprises a hydrocarbon sensor and an inclinometer.

16. The system of claim 10, wherein each of the plurality of sensors comprises a pH sensor, an inclinometer, and a hydrocarbon sensor.

17. The system of claim 10, wherein the receiving device is positionable in a well tool.

* * * * *